United States Patent
Zhou et al.

(10) Patent No.: US 10,626,118 B2
(45) Date of Patent: Apr. 21, 2020

(54) PYRROLOPYRIMIDINE CRYSTAL FOR PREPARING JAK INHIBITOR

(71) Applicants: Chia Tai Tianqing Pharmaceutical Group Co., Ltd., Lianyungang (CN); Lianyungang Runzhong Pharmaceutical Co., Ltd., Lianyungang (CN); Centaurus Biopharma Co., Ltd., Beijing (CN)

(72) Inventors: Zhou Zhou, Lianyungang (CN); Aiming Zhang, Lianyungang (CN); Xiquan Zhang, Lianyungang (CN); Huadong Yao, Lianyungang (CN)

(73) Assignees: CHIA TAI TIANQING PHARMACEUTICAL GROUP CO., LTD. (CN); LIANYUNGANG RUNZHONG PHARMACEUTICAL CO., LTD. (CN); CENTAURUS BIOPHARMA CO., LTD. (CN)

( * ) Notice: Subject to any disclaimer, the term of this patent is extended or adjusted under 35 U.S.C. 154(b) by 0 days.

(21) Appl. No.: 16/310,369

(22) PCT Filed: Jun. 15, 2017

(86) PCT No.: PCT/CN2017/088429
§ 371 (c)(1),
(2) Date: Dec. 14, 2018

(87) PCT Pub. No.: WO2017/215630
PCT Pub. Date: Dec. 21, 2017

(65) Prior Publication Data
US 2019/0330215 A1    Oct. 31, 2019

(30) Foreign Application Priority Data

Jun. 16, 2016 (CN) .......................... 2016 1 0435947

(51) Int. Cl.
C07D 487/04 (2006.01)
A61P 35/00 (2006.01)
B01D 9/00 (2006.01)

(52) U.S. Cl.
CPC ............ *C07D 487/04* (2013.01); *A61P 35/00* (2018.01); *B01D 9/005* (2013.01); *C07B 2200/13* (2013.01)

(58) Field of Classification Search
CPC ...... C07D 487/04; A61K 31/519; A61P 35/00
USPC ....................................... 544/280; 514/265.1
See application file for complete search history.

(56) References Cited

FOREIGN PATENT DOCUMENTS

| CN | 103214483 A | 7/2013 |
|---|---|---|
| CN | 105777754 A | 7/2016 |
| EP | 3 235 819 A1 | 10/2017 |
| WO | WO 2016/026975 A1 | 2/2016 |
| WO | WO 2016/095805 A1 | 6/2016 |
| WO | WO 2007/070514 A1 | 6/2017 |
| WO | WO 2017/215630 A1 | 12/2017 |

OTHER PUBLICATIONS

Pearce et al., Failure modes in anticancer drug discovery and development, Cancer Drug Design and Discovery Edited by Stephen Neidle, Chapter 18, pp. 424-435 (2008).*
Gura, Systems for identifying new drugs are often faulty, Science, Nov. 7, 1997, 278(5340): 1041-2.*
Johnson et al., Relationships between drug activity in NCI preclinical in vitro and in vivo models and early clinical trials, Br J Cancer. May 18, 2001, 84(10): 1424-31.*
Simone, Introduction, Omenn, Cancer Prevention, Part XIV. Oncology, Cecil Textbook of Medicine, 20th Edition, vol. 1, pp. 1004-1010 (1996).*

(Continued)

*Primary Examiner* — Deepak R Rao
(74) *Attorney, Agent, or Firm* — Weaver Austin Villeneuve & Sampson LLP (57) ABSTRACT

The present application relates to the field of pharmaceutical chemistry. The application specifically relates to a crystal form A and crystal form B of a pyrrolopyrimidine (formula I) for preparing a JAK inhibitor. The application further relates to a method for preparing the crystal form A and crystal form B, a crystalline composition comprising the crystal form A or crystal form B, a pharmaceutical composition comprising the crystal form A, crystal form B, or crystalline composition, and a pharmaceutical application of the pharmaceutical composition, the crystal form A, and the crystal form B. The crystal form A and crystal form B of the application has the advantages of high purity, high crystallinity, and good stability.

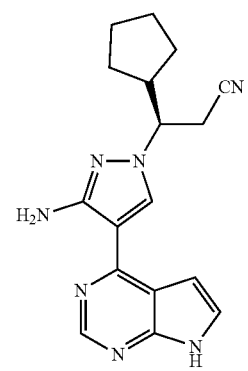

20 Claims, 3 Drawing Sheets (56) References Cited

OTHER PUBLICATIONS

Loriaux et al., High-throughput sequence analysis of the tyrosine kinome in acute myeloid leukemia, Blood, vol. 111, No. 9, pp. 4788-4796, 2008.*
International Search Report, with English Translation, and Written Opinion of the Searching Authority, dated Sep. 12, 2017 issued in Application No. PCT/CN2017/088429.
CN First Office Action dated Nov. 28, 2019 issued in CN Application No. 201780037131.9. (No translation available).
CN Search Report dated Jun. 15, 2017 issued in CN Application No. 2017800371319 (No translation available).
Chen, E. et al., "Janus Kinase Deregulation in Leukemiaand Lymphoma," Immunity 36, Elsevier Inc., Apr. 20, 2012, pp. 534-541.
Extended European Search Report dated Jan. 21, 2020 in EP Application No. 17812741.1.

* cited by examiner

PYRROLOPYRIMIDINE CRYSTAL FOR PREPARING JAK INHIBITOR

CROSS-REFERENCE TO RELATED APPLICATION

This application is under 37 U.S.C. §371 a national stage application of PCT application PCT/CN2017/088429, filed on Jun. 15, 2017, which claims the priority and benefit of the Chinese Patent Application No. 201610435947.4 filed at the China National Intellectual Property Administration on Jun. 16, 2016; all of the above prior applications are incorporated by reference in their entireties for all purposes.

TECHNICAL FIELD

The present application belongs to the field of medical chemistry. Specifically, the present application relates to a crystal of a pyrrolopyrimidine compound (3R)-3-[3-amino-4-(7H-pyrrolo[2,3-d]pyrimidin-4-yl)-1H-pyrazol-1-yl]-3-cyclopentyl-propionitrile as a JAK inhibitor, a crystalline composition, a pharmaceutical composition, a preparation method and use thereof.

BACKGROUND ART

Janus kinase (JAK) is a non-receptor type of tyrosine kinases (PTKs), which resides in cells and transduces cytokine stimulation signal via JAK-STAT pathway. By JAK-STAT pathway, a chemical signal outside the cell is transduced into a gene promoter on endonuclear DNA through cell membrane, and finally affects the DNA in cell to change its transcription and activity level. JAK-STAT pathway mainly consists of three components: (1) a receptor; (2) Janus kinase (JAK) and (3) a signal transducer and activator of transcription (STAT) protein. The receptor can be activated by interferon, interleukin, growth factor or other chemical messenger, and such activation leads to the phosphorylation of JAK itself. Then, the STAT protein bonds to the phosphorylated receptor, so that STAT is phosphorylated by JAK. After that, the phosphorylated STAT protein is isolated from the receptor, then dimerized and translocated into cell nucleus, thereby bonding to specific DNA site and changing transcription (Scott, M. J., C. J. Godshall et al. (2002). "Jaks, STATs, Cytokines, and Sepsis" Clin Diagn Lab Immunol 9(6): 1153-9).

JAK family plays a role in the cytokine-dependent regulation of proliferation and function of cells involved in immune response. At present, there are four known mammalian JAK family members: JAK1, JAK2, JAK3 and TYK2 (Tyrosine kinase 2). The JAK proteins have a size ranging from 120 kDa to 140 kDa, and comprise 7 conserved JAK homology (JH) domains. One of them is a functional catalytic kinase domain, and another is a pseudokinase domain which effectively exerts a regulatory function and/or acts as a docking site for STATs (Scott, Godshall et al. 2002, supra).

At present, various Janus kinase inhibitors have been reported. The Chinese patent application No. 201410784461.2 with the filing date of Dec. 16, 2014 discloses several JAK inhibitors (the contents of which are incorporated herein by reference in their entirety), including (3R)-3-[3-amino-4-(7H-pyrrolo[2,3-d]pyrimidin-4-yl)-1H-pyrazol-1-yl]-3-cyclopentyl-propionitrile compound represented by formula I:

In addition to therapeutic efficacy, drug developers attempt to provide a suitable form of an active molecule having properties as a drug. From the viewpoint of obtaining a commercially viable production method or from the viewpoint of producing a pharmaceutical composition comprising an active compound, the chemical stability, solid-state stability and shelf life of an active ingredient are very important factors. Therefore, it is very important for the development of a drug to provide a suitable form of the drug having desired properties.

SUMMARY OF THE INVENTION

In one aspect, the present application provides a crystal A of a compound represented by formula I, wherein an X-ray diffraction (XRD) pattern of the crystal A of the compound represented by formula I has diffraction peaks at 2θ of 9.35°±0.2°, 11.93°±0.2°, 16.32°±0.2°, 21.23°±0.2°, 23.13°±0.2° and 25.58°±0.2°.

In another aspect, the present application provides a method for preparing the crystal A of the compound represented by formula I, and the method comprises the following steps:

1) dissolving the compound represented by formula I in a crystallization solvent, wherein the crystallization solvent is selected from methanol, ethanol, n-propanol, isopropanol, n-butanol, isobutanol, t-butanol, ethylene glycol monomethyl ether, diethyl ether, isopropyl ether, methyl t-butyl ether, dioxane, tetrahydrofuran, 2-methyltetrahydrofuran, acetone, 1-butanone, 2-butanone, ethyl acetate, ethyl formate, methyl acetate, isopropyl acetate, dichloromethane, chloroform, water, or a mixed solvent of any two or more of the above solvents; and

2) crystallizing the compound represented by formula I.

In another aspect, the present application provides a crystalline composition, wherein the crystal A of the compound represented by formula I accounts for 50% or more, preferably 80% or more, more preferably 90% or more, and most preferably 95% or more, by weight of the crystalline composition.

In another aspect, the present application provides a pharmaceutical composition, wherein the pharmaceutical composition comprises an effective amount of the crystal A of the compound represented by formula I, or the crystalline composition comprising the crystal A of the compound represented by formula I.

In another aspect, the present application provides use of the crystal A of the compound represented by formula I, or the crystalline composition, or the pharmaceutical composition as described above in the preparation of a medicament for treating or preventing a Janus kinase-mediated disease.

In another aspect, the present application provides a crystal B of a compound represented by formula I, wherein an X-ray diffraction (XRD) pattern of the crystal B of the compound represented by formula I has diffraction peaks at 2θ of 8.97°±0.2°, 9.39°±0.2°, 12.90°±0.2°, 17.70°±0.2°, 20.31° 0.2° and 23.63°±0.2°.

In another aspect, the present application provides a method for preparing the crystal B of the compound represented by formula I, and the method comprises the following steps:

1) dissolving the compound represented by formula I in acetonitrile; and 2) crystallizing the compound represented by formula I.

In another aspect, the present application provides a crystalline composition, wherein the crystal B of the compound represented by formula I accounts for 50% or more, preferably 80% or more, more preferably 90% or more, and most preferably 95% or more, by weight of the crystalline composition.

In another aspect, the present application provides a pharmaceutical composition, wherein the pharmaceutical composition comprises an effective amount of the crystal B of the compound represented by formula I, or the crystalline composition comprising the crystal B of the compound represented by formula I.

In another aspect, the present application provides use of the crystal B of the compound represented by formula I, or the crystalline composition or the pharmaceutical composition as described above in the preparation of a medicament for treating or preventing a Janus kinase-mediated disease.

DETAILED DESCRIPTION OF THE INVENTION

In one aspect, the present application provides a crystal A of a compound represented by formula I:

wherein an X-ray diffraction (XRD) pattern of the crystal A of the compound represented by formula I has diffraction peaks at 2θ of 9.35°, 11.93°, 16.32°, 21.23°, 23.13° and 25.58°±0.2°; typically has diffraction peaks at 2θ of 9.35°, 11.93°, 16.32°, 18.82°, 20.54°, 21.23°, 23.13° and 25.58°±0.2°; more typically has diffraction peaks at 2θ of 9.35°, 10.93°, 11.93°, 14.46°, 16.32°, 18.82°, 20.54°, 21.23°, 21.66°, 23.13°, 25.58° and 26.34°±0.2°; and further typically has diffraction peaks at 2θ of 9.35°, 10.93°, 11.93°, 14.46°, 16.32°, 17.28°, 18.82°, 19.25°, 20.54°, 21.23°, 21.66°, 22.15°, 23.13°, 24.09°, 25.58° and 26.34°±0.2°.

In some embodiments of the present application, in an X-ray diffraction (XRD) pattern of the crystal A of the compound represented by formula I of the present application, the peak having the highest relative intensity appears at the position of the diffraction peak at 2θ of 11.93°, 16.32°, or 21.23°±0.2°; and preferably, the peak having the highest relative intensity appears at the position of the diffraction peak at 2θ of 11.93°±0.2°.

In some embodiments of the present application, in an X-ray diffraction (XRD) pattern of the crystal A of the compound represented by formula I of the present application, the peaks having top three relative intensities appear at the positions of diffraction peaks at 2θ of 9.35°, 11.93°, 16.32°, 21.23°, 23.13°, or 25.58°±0.2°.

In some embodiments of the present application, X-ray diffraction peaks of the crystal A of the compound represented by formula I of the present application have the following characteristics:

| Serial No. | 2θ ± 0.2 (°) | Relative Intensity (%) |
| --- | --- | --- |
| 1 | 9.35 | 43.1 |
| 2 | 10.82 | 16.0 |
| 3 | 10.93 | 17.0 |
| 4 | 11.93 | 100.0 |
| 5 | 13.65 | 15.8 |
| 6 | 14.46 | 18.6 |
| 7 | 16.32 | 58.1 |
| 8 | 17.28 | 13.9 |
| 9 | 18.82 | 40.9 |
| 10 | 19.25 | 22.3 |
| 11 | 20.54 | 41.6 |
| 12 | 21.23 | 75.9 |
| 13 | 21.66 | 38.1 |
| 14 | 22.15 | 26.9 |
| 15 | 23.13 | 55.5 |
| 16 | 23.47 | 14.5 |
| 17 | 24.09 | 23.5 |
| 18 | 25.58 | 54.3 |
| 19 | 26.34 | 33.8 |
| 20 | 30.02 | 15.8 |

Figure 1:
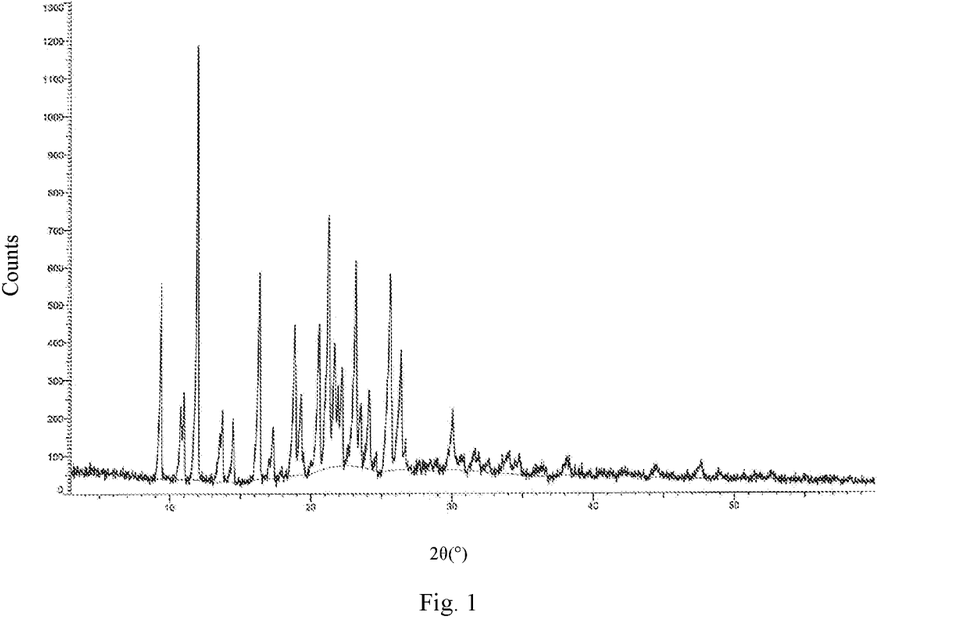
FIG. 1 is an XRD pattern of the crystal A of the compound represented by formula I (Method 1 in Example 2).

In some embodiments of the present application, an X-ray diffraction pattern of the crystal A of the compound represented by formula I is shown as FIG. 1.

Figure 2:
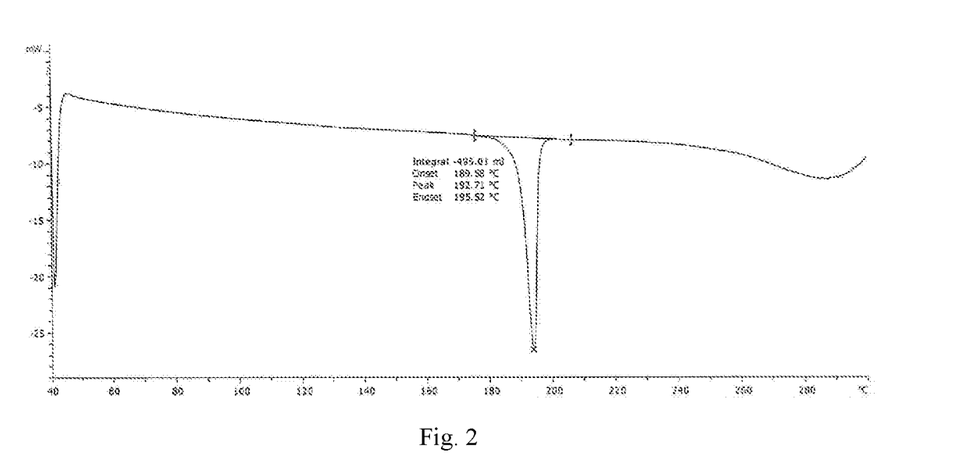
FIG. 2 is a DSC spectrum of the crystal A of the compound represented by formula I (Method 1 in Example 2).

In some embodiments of the present application, a DSC spectrum of the crystal A of the compound represented by formula I is shown as FIG. 2.

Figure 3:
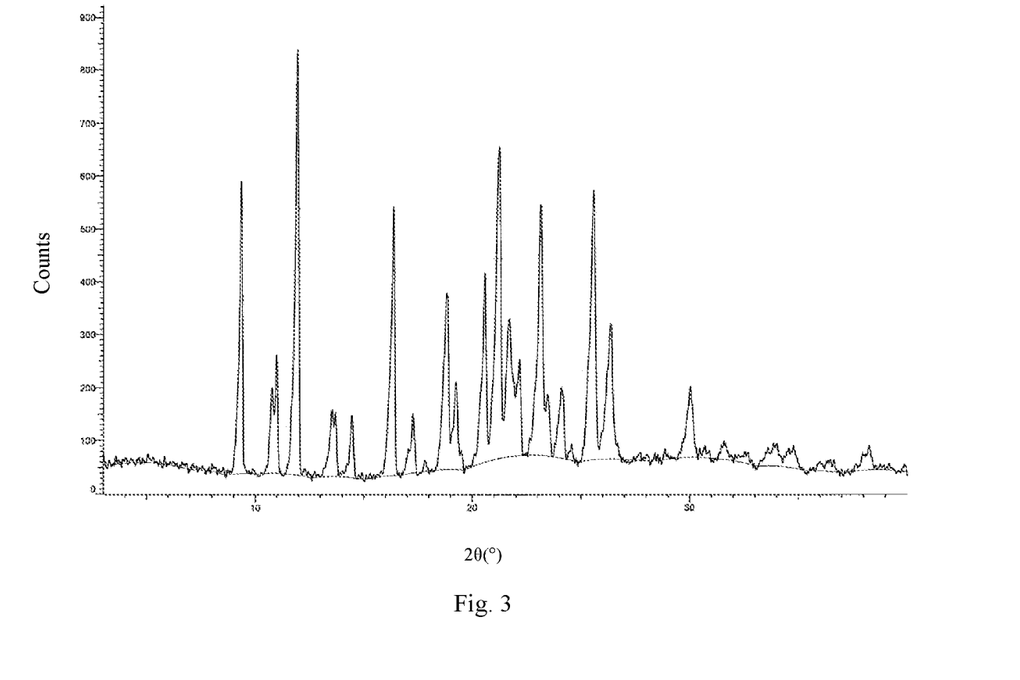
FIG. 3 is an XRD pattern of the crystal A of the compound represented by formula I (Method 2 in Example 2, ethanol-ethyl acetate (4:1)).

In some embodiments of the present application, an X-ray diffraction pattern of the crystal A of the compound represented by formula I is shown as FIG. 3.

Figure 4:
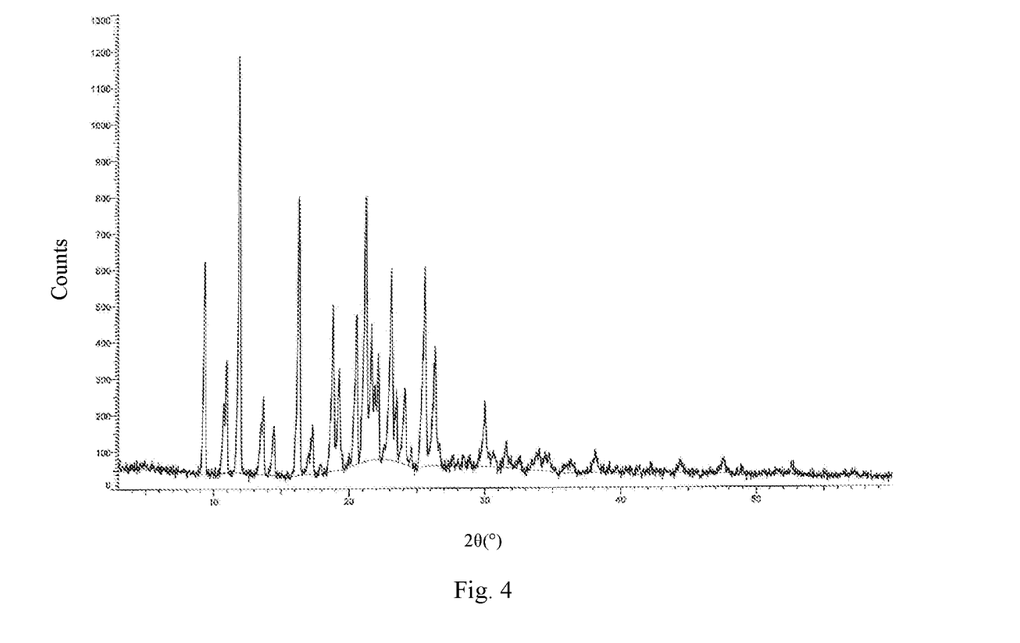
FIG. 4 is an XRD pattern of the crystal A of the compound represented by formula I (Method 3 in Example 2).

In some embodiments of the present application, an X-ray diffraction pattern of the crystal A of the compound represented by formula I is shown as FIG. 4.

In another aspect, the present application provides a method for preparing the crystal A of the compound represented by formula I, and the method comprises the following steps:

1) dissolving the compound represented by formula I in a crystallization solvent, wherein the crystallization solvent is selected from methanol, ethanol, n-propanol, isopropanol, n-butanol, isobutanol, t-butanol, ethylene glycol monomethyl ether, diethyl ether, isopropyl ether, methyl t-butyl ether, dioxane, tetrahydrofuran, 2-methyltetrahydrofuran, acetone, 1-butanone, 2-butanone, ethyl acetate, ethyl formate, methyl acetate, isopropyl acetate, dichloromethane, chloroform, water, or a mixed solvent of any two or more of the above solvents; and 2) crystallizing the compound represented by formula I, and optionally filtrating, washing, and/or drying the obtained solid.

In some embodiments of the present application, the crystallization solvent for preparing the crystal A of the compound represented by formula I is ethanol, isopropyl ether, ethyl acetate, acetone, dichloromethane, water, or a mixed solvent of any two or more of the above solvents; and preferably ethanol, a mixed solvent of ethanol and ethyl acetate, a mixed solvent of ethanol and water, a mixed solvent of ethanol and isopropyl ether, acetone, ethyl acetate, or dichloromethane.

In some embodiments of the present application, the crystallization solvent for preparing the crystal A of the compound represented by formula I is preferably ethanol or a mixed solvent comprising ethanol; and more preferably, the other solvent in the mixed solvent comprising ethanol is selected from methanol, n-propanol, isopropanol, n-butanol, isobutanol, t-butanol, ethylene glycol monomethyl ether, diethyl ether, isopropyl ether, methyl t-butyl ether, dioxane, tetrahydrofuran, 2-methyltetrahydrofuran, acetone, 1-butanone, 2-butanone, ethyl acetate, ethyl formate, methyl acetate, isopropyl acetate, dichloromethane, chloroform, or water.

In some embodiments of the present application, in the preparation of the crystal A of the compound represented by formula I, a ratio of the amount of the compound represented by formula I (by weight, in the unit of g) to the amount of the crystallization solvent (by volume, in the unit of mL) is in the range of 1:5 to 1:50, preferably 1:7.5, 1:10, 1:12, 1:15, 1:18, 1:20, 1:25, 1:30, 1:35, 1:40, 1:45, or 1:50, and more preferably 1:7.5 to 1:30.

In some embodiments of the present application, when the crystallization solvent for preparing the crystal A of the compound represented by formula I is a mixed solvent comprising ethanol, the content of ethanol (by volume) is 10% to 90%; and preferably 10%, 20%, 25%, 30%, 33%, 40%, 50%, 60%, 66%, 70%, 75%, 80%, or 90%.

In some embodiments of the present application, when the crystallization solvent for preparing the crystal A of the compound represented by formula I is a mixed solvent comprising ethanol, a ratio of ethanol to the other solvent (by volume) is in the range of 9:1 to 1:9; and preferably 9:1, 8:1, 7:1, 6:1, 5:1, 4:1, 3:1, 2:1, 1:1, 1:2, 1:3, 1:4, 1:5, 1:6, 1:7, 1:8, or 1:9.

In some embodiments of the present application, crystallization may be implemented by cooling, e.g., cooling to 0° C. to 5° C. for crystallization. In some embodiments of the present application, crystallization may be implemented by concentration under reduced pressure.

In another aspect, the present application provides a crystalline composition comprising the crystal A of the compound represented by formula I. In some embodiments of the present application, the crystal A of the compound represented by formula I accounts for 50% or more, preferably 80% or more, more preferably 90% or more, and most preferably 95% or more, by weight of the crystalline composition.

In another aspect, the present application provides a pharmaceutical composition comprising the crystal A of the compound represented by formula I, wherein the pharmaceutical composition comprises an effective amount of the crystal A of the compound represented by formula I, or the crystalline composition comprising the crystal A of the compound represented by formula I. Furthermore, the pharmaceutical composition may or may not further comprise a pharmaceutically acceptable carrier, excipient, and/or medium.

In another aspect, the present application provides use of the crystal A of the compound represented by formula I, or the crystalline composition, or the pharmaceutical composition as described above in the preparation of a medicament for treating or preventing a Janus kinase-mediated disease.

In another aspect, the present application provides a method for treating or preventing a Janus kinase-mediated disease, comprising administering to a mammal in need thereof a therapeutically effective amount of the crystal A of the compound represented by formula I, or the crystalline composition, or the pharmaceutical composition as described above.

In another aspect, the present application provides the crystal A of the compound represented by formula I, or the crystalline composition, or the pharmaceutical composition as described above for use in treating or preventing a Janus kinase-mediated disease.

In another aspect, the present application provides a crystal B of a compound represented by formula I:

I wherein an X-ray diffraction (XRD) pattern of the crystal B of the compound represented by formula I has diffraction peaks at 2θ of 8.97°, 9.39°, 12.90°, 17.70°, 20.31° and 23.63°±0.2°; typically has diffraction peaks at 2θ of 8.97°, 9.39°, 12.90°, 16.54°, 17.70°, 19.20°, 20.31°, 22.78° and 23.63°±0.2°; and more typically has diffraction peaks at 2θ of 8.97°, 9.39°, 11.24°, 12.90°, 14.56°, 16.54°, 17.70°, 19.20°, 20.31°, 22.23°, 22.78°, 23.63° and 25.55°±0.2°.

In some embodiments of the present application, in an X-ray diffraction (XRD) pattern of the crystal B of the compound represented by formula I of the present application, the peak having the highest relative intensity appears at the position of the diffraction peak at 2θ of 9.39°, 17.70°, or 23.63°±0.2°; and preferably, the peak having the highest relative intensity appears at the position of the diffraction peak at 2θ of 17.70°±0.2°.

In some embodiments of the present application, X-ray diffraction peaks of the crystal B of the compound represented by formula I of the present application have the following characteristics:

| Serial No. | 2θ ± 0.2 (°) | Relative Intensity (%) |
|---|---|---|
| 1 | 8.97 | 40.7 |
| 2 | 9.39 | 47.4 |
| 3 | 11.24 | 17.9 |
| 4 | 12.90 | 34.4 |
| 5 | 12.96 | 32.8 |
| 6 | 14.56 | 14.4 |
| 7 | 16.54 | 22.1 |
| 8 | 17.15 | 40.4 |
| 9 | 17.70 | 100.0 |
| 10 | 19.20 | 24.4 |
| 11 | 20.31 | 36.1 |
| 12 | 20.41 | 24.3 |
| 13 | 21.03 | 21.3 |
| 14 | 21.96 | 18.6 |
| 15 | 22.23 | 18.9 |
| 16 | 22.78 | 23.1 |
| 17 | 23.50 | 46.9 |
| 18 | 23.63 | 65.0 |
| 19 | 25.55 | 17.3 |

Figure 5:
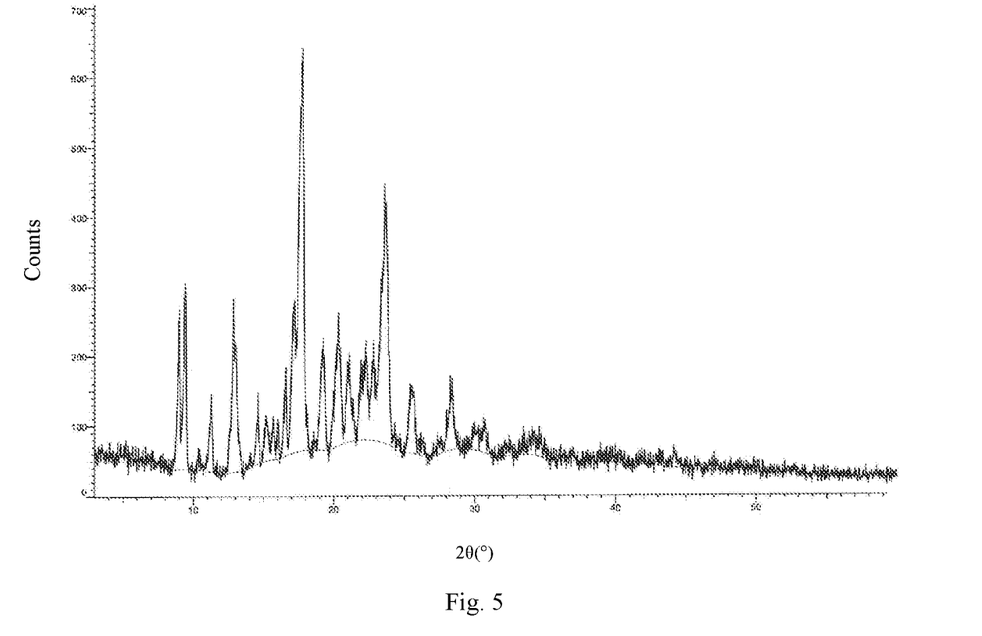
FIG. 5 is an XRD pattern of the crystal B of the compound represented by formula I (Example 3).

In some embodiments of the present application, an X-ray diffraction pattern of the crystal B of the compound represented by formula I is shown as FIG. 5.

Figure 6:
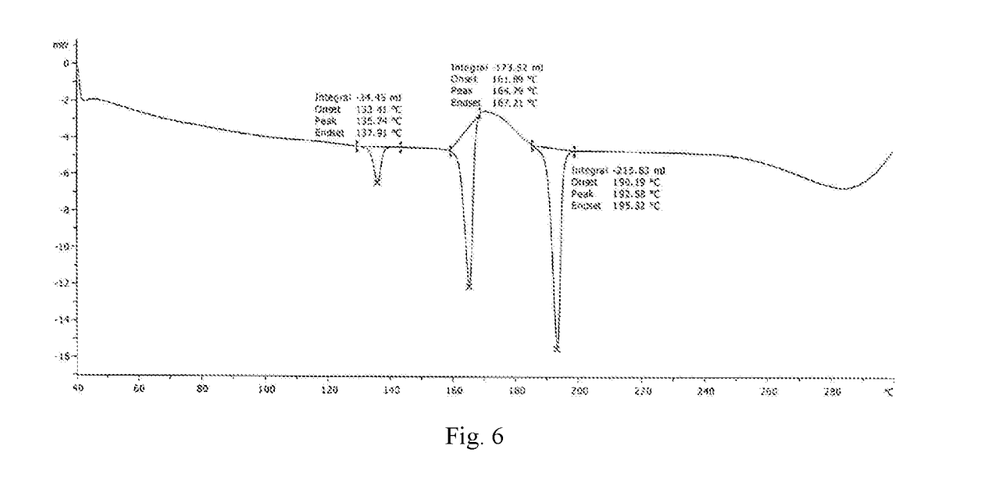
FIG. 6 is a DSC spectrum of the crystal B of the compound represented by formula I (Example 3).

In some embodiments of the present application, a DSC spectrum of the crystal B of the compound represented by formula I is shown as FIG. 6.

The crystal B of the compound represented by formula I according to the present application is an acetonitrilate of the compound represented by formula I, wherein a molar ratio of the compound represented by formula I to acetonitrile is in the range of 1:0.5 to 1:2.0, and is preferably 1:0.5, 1:1, 1:1.5, or 1:2.0.

In another aspect, the present application provides a method for preparing the crystal B of the compound represented by formula I and the method comprises the following steps:

1) dissolving the compound represented by formula I in acetonitrile; and 2) crystallizing the compound represented by formula I, and optionally filtrating, washing, and/or drying the obtained solid.

In some embodiments of the present application, in the preparation of the crystal B of the compound represented by formula I, a ratio of the amount of the compound represented by formula I (by weight, in the unit of g) to the amount of the crystallization solvent acetonitrile (by volume, in the unit of mL) is in the range of 1:5 to 1:50, preferably 1:7.5, 1:10, 1:12, 1:15, 1:18, 1:20, 1:25, 1:30, 1:35, 1:40, 1:45, or 1:50, and more preferably in the range of 1:10 to 1:25.

In some embodiments of the present application, the crystallization may be implemented by cooling, e.g., by cooling to 0° C. to 5° C. for crystallization.

In another aspect, the present application provides a crystalline composition comprising the crystal B of the compound represented by formula I. In some embodiments of the present application, the crystal B of the compound represented by formula I accounts for 50% or more, preferably 80% or more, more preferably 90% or more, and most preferably 95% or more, by weight of the crystalline composition.

In another aspect, the present application provides a pharmaceutical composition comprising the crystal B of the compound represented by formula I, wherein the pharmaceutical composition comprises an effective amount of the crystal B of the compound represented by formula I, or the crystalline composition comprising the crystal B of the compound represented by formula I. Furthermore, the pharmaceutical composition may or may not further comprise a pharmaceutically acceptable carrier, excipient, and/or medium.

In another aspect, the present application provides use of the crystal B of the compound represented by formula I, or the crystalline composition, or the pharmaceutical composition as described above in the preparation of a medicament for treating or preventing a Janus kinase-mediated disease.

In another aspect, the present application provides a method for treating or preventing a Janus kinase-mediated disease, comprising administering to a mammal in need thereof a therapeutically effective amount of the crystal B of the compound represented by formula I, or the crystalline composition, or the pharmaceutical composition as described above.

In another aspect, the present application provides the crystal B of the compound represented by formula I, or the crystalline composition, or the pharmaceutical composition as described above for use in treating or preventing a Janus kinase-mediated disease.

In the present application, the X-ray diffraction patterns are measured by the following method: instrument: Bruker D8 ADVANCE X-ray diffractometer; method: target: Cu: K-Alpha; wavelength λ=1.54179 Å; tube voltage: 40 kV; tube current: 40 mA; scan range: 4-40°; scanning speed: 0.1 sec/step, 0.02°/step.

In the present application, the following method for differential scanning calorimetry (DSC) is used: instrument: Mettler DSC-1 differential scanning calorimeter; method:

samples (~5 mg) are tested in an aluminum pan for DSC at 30° C. to 300° C., and at a heating rate of 10° C./min.

It should be noted that, in an X-ray diffraction spectrum, a diffraction pattern of a crystalline compound is usually characteristic for a specific crystalline form. Relative intensities of the bands (especially at the low angles) can vary depending upon preferential orientation effects resulting from the differences of crystals' conditions, particle sizes, and other measuring conditions. Therefore, the relative intensities of diffraction peaks are not characteristic for a specific crystalline form. It is the relative positions of peaks rather than relative intensities thereof that should be paid more attention when judging whether a crystalline form is the same as a known crystalline form. In additional, as for any given crystalline form, there may be a slight error in the position of peaks, which is also well known in the field of crystallography. For example, the position of a peak may shift due to the change of a temperature, the movement of a sample or the calibration of an instrument and so on when analyzing the sample, and the measurement error of 2θ value is sometimes about ±0.2°. Accordingly, this error should be taken into consideration when identifying a crystal structure. Usually, the position of a peak is expressed in terms of 2θ angle or lattice spacing d in an XRD pattern and the simple conversion relationship therebetween is d=λ/2 sin θ, wherein d represents the lattice spacing, k represents the wavelength of incident X-ray, and θ represents the diffraction angle. For the same crystalline form of the same compound, the position of peaks in an XRD spectrum thereof has similarity on the whole, and the error of relative intensities may be larger. In addition, it is necessary to point out that due to some factors such as reduced contents, parts of diffraction lines may be absent in the identification of a mixture. At this time, even a band may be characteristic for the given crystalline form without depending upon all the bands of a high purity sample.

It should be noted that DSC is used to measure a thermal transition temperature when absorbing or releasing heat due to the change of a crystal structure or the melting of a crystal. In a continuous analysis of the same crystalline form of the same compound, the error of a thermal transition temperature and a melting point is typically within a range of about ±5° C. When it is said that a compound has a given DSC peak or melting point, it means that the DSC peak or melting point may be varied within a range of ±5° C. DSC provides an auxiliary method to distinguish different crystalline forms. Different crystalline forms can be identified by their characteristically different transition temperatures.

The Janus kinase-mediated disease according to the present application includes, but is not limited to, a tumor (e.g., lymphoma, leukemia). The lymphoma according to the present application includes, but is not limited to, Hodgkin's disease or non-Hodgkin's lymphoma, and the non-Hodgkin's lymphoma includes, but is not limited to, B-cell lymphoma or T-cell lymphoma. The leukemia according to the present application includes, but is not limited to, acute lymphoblastic leukemia, chronic lymphocytic leukemia, acute myeloid leukemia, and chronic myelocytic leukemia.

In the present application, the term "pharmaceutical composition" refers to a formulation of one or more compounds of the present application and a carrier, an excipient, and/or a medium generally accepted in the art for transporting a bioactive compound to an organism (e.g., human). An object of the pharmaceutical composition is to facilitate administering the compound of the present application to an organism.

The term "carrier" is defined as a compound that facilitates introducing a compound into a cell or tissue. For example, dimethyl sulfoxide (DMSO) is commonly used as a carrier, because it is easy to use it to introduce some organic compounds into cells or tissues of organisms.

The term "pharmaceutically acceptable carrier" includes, but is not limited to, any adjuvant, excipient, glidant, sweetener, diluent, preservative, dye/colorant, flavoring agent, surfactant, wetting agent, dispersant, suspension agent, stabilizer, isotonic agent, solvent, or emulsifier approved by the National Drug Administration as acceptable for use in human or livestocks.

The term "therapeutically effective amount" refers to an amount of the compound of the present application, and when it is administered to a mammal, preferably human, it is enough to realize the treatment of viral infection in a mammal, preferably in human, as defined hereinafter. The amount of the compound of the present application forming the "therapeutically effective amount" changes with the compound, the disease condition and its severity, the administration route, and the age of the mammal to be treated, but can be conventionally determined by those with ordinary skills in the art based on their own knowledge and the disclosure of the present application.

The term "treatment" used herein covers the treatment of viral infection in mammal, preferably viral infection in human, and comprises:

(i) inhibiting viral infection, i.e., arresting its development;

(ii) alleviating viral infection; i.e., causing regression of the viral infection; or (iii) alleviating symptoms caused by viral infection.

All solvents used in the present application are available on the market, and can be used without further purification. The reactions are generally carried out in an inert nitrogen atmosphere in an anhydrous solvent.

In the present application, the proton nuclear magnetic resonance data are recorded in a BRUKER AVANCE III HD 500M spectrometer; the chemical shift is expressed in ppm downfield from tetramethylsilane; and the mass spectrum is measured by Waters ACQUITY UPLC+XEVO G2 QTof. The mass spectrometer is equipped with an electrospray ion source (ESI) operated in a positive or negative mode.

The crystal A and crystal B of the compound represented by formula I according to the present application have advantages of high purity, high crystallinity, and good stability. Furthermore, the methods for preparing the crystal A and the crystal B of the compound represented by formula I according to the present application are simple, the solvents used therein are inexpensive and easily available, and the crystallization conditions are mild. Therefore, the methods are suitable for industrial production.

The following examples are provided to further illustrate the technical solutions of the present application in a non-limiting manner. They should not be construed as limiting the scope of the present invention, but merely as illustrative description and typical representatives of the present invention. The solvents, reagents, and starting materials used in the present application are chemically pure or analytically pure products available on the market.

Example 1: (3R)-3-{3-amino-4-{7H-pyrrolo[2,3-d]pyrimidin-4-yl}-1H-pyrazol-1-yl}-3-cyclopentyl-propanenitrile (I)

Step A: 3-Cyclopentyl-acrylic acid

Cyclopentyl-carbaldehyde (344.4 g, 3.51 mol, 1.17 eq.) was added dropwise to a solution of 5M propandioic acid (312 g, 3.0 mol, 1.0 eq.) in pyridine at room temperature. After the completion of the addition, the resulting mixture was stirred for 10 minutes. Then, piperidine (6.2 g, 0.075 mol, 0.025 eq.) was slowly added dropwise. After the completion of the addition, the resulting mixture was stirred at room temperature for 1 hour. The resulting mixture was heated to 70° C. to 80° C., stirred for 8 hours, and concentrated under reduced pressure to evaporate the solvent. The residue was adjusted with concentrated hydrochloric acid to pH 3.0, and extracted with ethyl acetate three times. The organic phases were combined, and washed with 2.5M sodium hydroxide solution five times. The aqueous phase was adjusted with concentrated hydrochloric acid to pH 3.0, and extracted with ethyl acetate three times. The organic layers were combined, washed with water three times, washed with saturated salt solution, dried with anhydrous sodium sulfate, filtered, and concentrated under reduced pressure to obtain 3-cyclopentyl-acrylic acid (391.2 g, yield: 93%). $^1$H NMR (500 MHz, CDCl$_3$) δ:7.08 (dd, J=15.6, 8.1 Hz, 1H), 5.81 (dd, J=15.6, 1.1 Hz, 1H), 11.25 (s, 1H), 2.64 (m, 1H), 1.63 (m, 2H), 1.42 (m, 2H), 1.86 (m, 2H), 1.72 (m, 2H); HRMS (ESI) calcd. for C$_8$H$_{12}$O$_2$[M−H]$^-$ 139.0765; Found: 139.0760.

Step B: 5-Cyclopentyl-pyrazolidin-3-one

80% Hydrazine hydrate (253.5 g, 4.05 mol, 1.5 eq.) was added dropwise to cyclopentyl-acrylic acid (378 g, 2.7 mol, 1.0 eq.) under stirring at room temperature. The resulting mixture was heated to 70° C. to 80° C., stirred for 6 hours, cooled to 0° C. to 10° C., stirred for crystallization, and filtered. The filter cake was washed with water twice, and dried under forced air at 45° C. for 12 hours to obtain 5-cyclopentyl-pyrazolidin-3-one (292.5 g, 68% yield).

Step C: R-5-cyclopentyl-pyrazolidin-3-one-D-tartrate

D-tartaric acid (135 g, 0.9 mol, 0.5 eq.) was added to a solution of 5-cyclopentyl-pyrazolidin-3-one (278 g, 1.8 mol, 1.0 eq.) in acetone under stirring at room temperature, stirred to react for 2 hours for crystallization, and filtered. The filter cake was refined with acetone 5 times, and dried under forced air at 50° C. to obtain R-5-cyclopentyl-pyrazolidin-3-one-D-tartrate (241 g, 88% yield, 99.5% ee value).

Step D: R-5-cyclopentyl-pyrazolidin-3-one

R-5-cyclopentyl-pyrazolidin-3-one-D-tartrate (228 g, 0.75 mol, 1.0 eq.) was added to a solution of 4M sodium hydroxide (52.2 g, 2.61 mol, 1.74 eq.) under stirring at room temperature, and the resulting mixture was extracted with dichloromethane. The organic layers were combined, dried with anhydrous magnesium sulfate, and filtered. The filtrate was concentrated under reduced pressure to obtain R-5-cyclopentyl-pyrazolidin-3-one (100.6 g, 85.2% yield, 99.5% ee value). $^1$H-NMR (500 MHz, CDCl$_3$) δ8.93 (s, 1H), 5.15 (s, 1H), 1.89 (m, 1H), 1.67 (m, 2H), 1.55 (m, 2H), 1.47 (m, 2H), 1.26 (m, 1H), 1.14 (m, 1H); HRMS (ESI) calcd. for C$_8$H$_{14}$N$_2$O [M+H]$^+$ 155.1179; Found: 155.1183.

Step E: 4-Chloro-7-{[2-(trimethylsilyl)ethoxy]methyl}-7H-pyrrolo[2,3-d]pyrimidine A solution of 4-chloropyrrolo[2,3-d]pyrimidine (200 g, 1.3 mol, 1.0 eq.) in N,N-dimethylformamide was added to 60% NaH (62.4 g, 1.56 mol, 1.2 eq.) in an ice bath. After the completion of the addition, the resulting mixture was stirred to react at room temperature for 1 hour. 2-(Trimethylsilyl)ethoxymethyl chloride (SEMCl, 260 g, 1.56 mol, 1.2 eq.) was slowly added dropwise under cooling in an ice bath. After the completion of the addition, the resulting mixture was stirred to react in an ice bath for 1 hour, and the reaction was quenched with water. The resulting mixture was extracted with ethyl acetate. The organic phases were combined, washed with saturated salt solution, dried with anhydrous sodium sulfate, and filtered. The filtrate was concentrated under reduced pressure to obtain a residue, which was purified by silica gel column chromatography to obtain 4-chloro-7-{[2-(trimethylsilyl)ethoxy]methyl}-7H-pyrrolo[2,3-d]pyrimidine (312.2 g, 91.8% yield). $^1$H-NMR (500 MHz, CDCl$_3$): δ8.64 (s, 1H), 7.38 (d, J=3.6 Hz, 1H), 6.65 (d, J=3.6 Hz, 1H), 5.64 (s, 2H), 3.52 (t, J=8.2 Hz, 2H), 0.90 (t, J=8.2 Hz, 2H), −0.07 (s, 9H); HRMS (ESI) calcd. for C$_{12}$H$_{18}$N$_3$OSi [M+H]$^+$ 284.0980; Found: 284.0995.

Step F: Ethyl 2-cyano-2-{7-{[2-(trimethylsilyl)ethoxy]methyl}-7H-pyrrolo[2,3-d]pyrimidin-4-yl}acetate

Potassium carbonate (207 g, 1.5 mol, 3.0 eq.) was added to a solution of 4-chloro-7-{[2-(trimethylsilyl)ethoxy]methyl}-7H-pyrrolo[2,3-d]pyrimidine (142 g, 0.5 mol, 1.0 eq.) and ethyl cyanoacetate (85 g, 0.75 mol, 1.5 eq.) in DMF under stirring at room temperature. The resulting mixture was heated to 120° C., stirred to react for 4 hours, and then cooled to room temperature. The reaction was quenched with water, stirred for crystallization, and filtered. The filter cake was washed with water, and dried under forced air at 50° C. to obtain ethyl 2-cyano-2-{7-{[2-(trimethylsilyl)ethoxy]methyl}-7H-pyrrolo [2,3-d]pyrimidin-4-yl}acetate (167 g, 92.6% yield). $^1$H-NMR (500 MHz, CDCl$_3$): δ13.46 (s, 1H), 8.45 (s, 1H), 7.56 (d, J=3.6 Hz, 1H), 7.18 (d, J=3.6 Hz, 1H), 5.56 (s, 2H), 4.32 (q, J=7.1 Hz, 2H), 3.52 (t, J=8.2 Hz, 2H), 1.27 (t, J=7.1 Hz, 3H), 0.83 (t, J=8.2 Hz, 2H), −0.08 (s, 9H); HRMS (ESI) calcd. for C$_{17}$H$_{24}$N$_4$O$_3$Si [M+H]$^+$ 361.1690; Found: 361.1699.

Step G: 2-{7-{[2-(Trimethylsilyl)ethoxy]methyl}-7H-pyrrolo[2,3-d]pyrimidin-4-yl)}acetonitrile Sodium chloride (263 g, 4.5 mol, 10 eq.) was added to a mixed solution of ethyl 2-cyano-2-{7-{[2-(trimethylsilyl)ethoxy]methyl}-7H-pyrrolo[2,3-d]pyrimidin-4-yl}acetate (162.2 g, 0.45 mol, 1.0 eq.) in N-methylpyrrolidone and water under stirring at room temperature. The resulting mixture was heated to 160° C. to 170° C., and stirred to react for 30 hours. The reaction was quenched with water. The resulting mixture was extracted with ethyl acetate. The organic phase was washed with saturated salt solution, dried with anhydrous sodium sulfate, filtered, and concentrated. The residue was purified by silica gel column chromatography to obtain 2-(7-{[2-(trimethylsilyl)ethoxy]methyl}-7H-pyrrolo[2,3-d]pyrimidin-4-yl)acetonitrile (98.6 g, 76% yield). $^1$H-NMR (500 MHz, CDCl$_3$): δ8.18 (s, 1H), 7.77 (d, J=3.4 Hz, 1H), 6.83 (d, J=3.4 Hz, 1H), 5.65 (s, 2H), 4.56 (s, 2H), 3.52 (t, J=7.6 Hz, 2H), 0.82 (t, J=7.6 Hz, 2H), −0.10 (s, 9H); HRMS (ESI) calcd. for C$_{14}$H$_{20}$N$_4$OSi [M+H]$^+$ 289.1479; Found: 289.1498.

Step H: 3-(Dimethylamino)-2-{7-{[2-(trimethylsilyl)ethoxy]methyl}-7H-pyrrolo[2,3-d]pyrimidin-4-yl}acrylonitrile DMF-DMA (119 g, 1.0 mol, 3.0 eq.) was added to a solution of 2-{7-{[2-(trimethylsilyl)ethoxy]methyl}-7H-pyrrolo[2,3-d]pyrimidin-4-yl}acetonitrile (95 g, 0.33 mol, 1.0 eq.) in DMF. The resulting mixture was heated to reflux to react for 2 hours, and then cooled to room temperature. Water was added, and the resulting mixture was stirred for crystallization, and filtered. The filter cake was washed with water, and dried under forced air at 50° C. to obtain 3-(dimethylamino)-2-(7-{[2-(trimethylsilyl)ethoxy]methyl}-7H-pyrrolo[2,3-d]pyrimidin-4-yl)acrylonitrile (106.5 g, 94% yield).

$^1$H-NMR (500 MHz, CDCl$_3$): δ8.50 (s, 1H), 8.38 (s, 1H), 7.26 (d, J=3.7 Hz, 1H), 7.18 (d, J=3.7 Hz, 1H), 5.56 (s, 2H), 3.49 (t, J=8.4 Hz, 2H), 3.43 (s, 3H), 3.23 (s, 3H), 0.87 (t, J=8.4 Hz, 2H), −0.10 (s, 9H); HRMS (ESI) calcd. for C$_{17}$H$_{25}$N$_5$OSi [M+H]$^+$ 344.1901; Found: 344.1907.

Step I: (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentyl-propionic acid

Potassium acetate (1.5 eq.) was added to a solution of 3-(dimethylamino)-2-{7-{[2-(trimethylsilyl)ethoxy]methyl}-7H-pyrrolo[2,3-d]pyrimidin-4-yl}acrylonitrile (68.7 g, 0.2 mol, 1.0 eq.) and R-5-cyclopentyl-pyrazolidin-3-one (37.0 g, 0.24 mol, 1.2 eq.) in N-methylpyrrolidone under stirring at room temperature. The resulting mixture was heated to 120° C. to 130° C., and stirred to react for 12 hours. The reaction was quenched with water, and the resulting mixture was extracted with ethyl acetate. The organic layer was washed with water three times, washed with saturated salt solution, and dried with anhydrous sodium sulfate. After filtration, a residue was obtained by concentration under reduced pressure, and purified by silica gel column chromatography to obtain (R)-3-{3-amino-4-{7-{[2-(trimethylsilyl)ethoxy]methyl}-7H-pyrrolo[2,3-d]pyrimidin-4-yl})-1H-pyrazol-1-yl}-3-cyclopentyl-propionic acid (37.6 g, 40.1% yield, ee value 99.8%). $^1$H-NMR (500 MHz, CDCl$_3$): δ8.74 (s, 1H), 7.96 (s, 1H), 7.32 (d, J=3.4 Hz, 1H), 6.67 (d, J=3.4 Hz, 1H), 5.63 (m, 2H), 4.19 (t, J=8.2 Hz, 2H), 3.52 (m, 1H), 3.52 (t, J=8.4 Hz, 2H), 3.09 (dd, J=16.7, 8.2 Hz, 1H), 2.87 (d, J=16.7 Hz, 1H), 2.41 (m, 1H), 1.87 (m, 1H), 1.69 (m, 1H), 1.60 (m, 2H), 1.51 (m, 2H), 1.15 (m, 1H), 0.91 (t, J=8.4 Hz, 2H), −0.06 (s, 9H); HRMS (ESI) calcd. for C$_{17}$H$_{25}$N$_5$OSi [M+H]$^+$ 471.2534; Found: 471.2538.

Step J: (R)-3-{3-(2,5-dioxopyrrol-1-yl)-4-{7-{[2-(trimethylsilyl)ethoxy]methyl}-7H-pyrrolo[2,3-d]pyrimidin-4-yl)}-1H-pyrazol-1-yl}-3-cyclopentyl-propionic acid Succinic anhydride (10.4 g, 104 mmol, 1.4 eq.) was added to a solution of 0.2 M (R)-3-{3-amino-4-{7-{[2-(trimethylsilyl)ethoxy]methyl}-7H-pyrrolo[2,3-d]pyrimidin-4-yl}-1H-pyrazol-1-yl}-3-cyclopentyl-propionic acid (35.0 g, 74.3 mmol, 1.0 eq.) in methylbenzene under stirring at room temperature. Under the protection of nitrogen gas, the resulting mixture was heated to reflux to react (water diversion) for 14 hours. The solvent was evaporated by concentration under reduced pressure. The residue was dissolved in ethyl acetate, and washed with water, a saturated sodium bicarbonate solution, and a saturated salt solution. The ethyl acetate layer was dried and decolorized with anhydrous sodium sulfate and activated carbon under stirring, filtered, and concentrated under reduced pressure to obtain (R)-3-{3-(2,5-dioxopyrrol-1-yl)-4-{7-{[2-(trimethylsilyl) ethoxy]methyl}-7H-pyrrolo[2,3-d]pyrimidin-4-yl}-1H-pyrazol-1-yl}-3-cyclopentyl-propionic acid (39 g, 70.6 mmol, 95% yield). $^1$H-NMR (500 MHz, CDCl$_3$): δ8.65 (s, 1H), 8.28 (s, 1H), 7.28 (d, J=3.7 Hz, 1H), 6.62 (d, J=3.7 Hz, 1H), 5.59 (d, J=11.1 Hz, 1H), 5.53 (d, J=11.1 Hz, 1H), 4.44 (td, J=9.9, 3.2 Hz, 1H), 3.48 (m, 2H), 3.02 (dd, J=16.8, 10.0 Hz, 1H), 2.83 (m, 1H), 2.43 (m, 1H), 1.78 (m, 1H), 1.69 (m, 1H), 1.61 (m, 1H), 1.52 (m, 1H), 1.51 (m, 1H), 1.50 (m, 2H), 1.14 (m, 1H), 0.88 (m, 2H), −0.07 (s, 9H); HRMS (ESI) calcd. for C$_{27}$H$_{36}$N$_6$O$_5$Si [M+H]$^+$ 553.2589; Found: 553.2603.

Step K: (R)-3-cyclopentyl-3-[3-(2,5-dioxopyrrol-1-yl)-4-(7-{[2-(trimethylsilyl) ethoxy]methyl}-7H-pyrrolo[2,3-d]pyrimidin-4-yl)-1H-pyrazol-1-yl]propanamide Oxalyl chloride (20.0 g, 158 mmol, 2.5 eq.) was added dropwise to a solution of 0.18 M (R)-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}-3-cyclopentyl-propionic acid (35.0 g, 63.3 mmol, 1.0 eq.) in dichloromethane under stirring in an ice bath and under the protection of nitrogen gas. After the completion of the addition, DMF (0.1 g, 1.3 mmol, 0.02 eq.) was added dropwise, and the resulting mixture was stirred at room temperature to react for 1 hour, and concentrated under reduced pressure to evaporate the solvent. The resulting mixture was dissolved in THF which was dried with sodium sticks and reevaporated, and the resulting mixture was added dropwise to a solution of 2M aqueous ammonia (20.0, 0.32 mol, 5.0 eq.) in THF. The resulting mixture was stirred in an ice bath to react for 30 minutes, concentrated under reduced pressure to evaporate THF, cooled in an ice bath for 2 hours for crystallization, and filtered. The filter cake was washed with water, and dried under forced air at 50° C. to obtain (R)-3-cyclopentyl-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}propanamide (29.8 g, 85.5% yield).

$^1$H-NMR (500 MHz, CDCl$_3$): δ8.65 (s, 1H), 8.24 (s, 1H), 7.32 (d, J=3.7 Hz, 1H), 6.63 (d, J=3.7 Hz, 1H), 6.12 (s, 1H), 5.60 (d, J=11.1 Hz, 1H), 5.56 (d, J=11.1 Hz, 1H), 5.44 (s, 1H), 4.40 (td, J=10.6, 3.2 Hz, 1H), 3.47 (dd, J=9.1, 7.5 Hz, 2H), 2.99 (dd, J=14.4, 11.0 Hz, 1H), 2.91 (s, 4H), 2.67 (dd, J=14.4, 3.3 Hz, 1H), 2.48 (m, 1H), 1.84 (m, 1H), 1.66 (m, 1H), 1.58 (m, 2H), 1.57 (m, 1H), 1.50 (m, 1H), 1.31 (m, 1H), 1.21 (m, 1H), 0.88 (dd, 9.1, 7.5, 2H), −0.08 (s, 9H); HRMS (ES) calcd. for C$_{27}$H$_{37}$N$_7$O$_4$Si [M+H]$^+$ 552.2749; Found: 552.2759.

Step L: (R)-3-cyclopentyl-3-[3-(2,5-dioxopyrrol-1-yl)-4-(7-{[2-(trimethylsilyl) ethoxy]methyl}-7H-pyrrolo[2,3-d]pyrimidin-4-yl)-1H-pyrazol-1-yl]propionitrile Phosphorus oxychloride (27.8 g, 181 mmol, 4.0 eq.) was added dropwise to a solution of 0.2 M (R)-3-cyclopentyl-3-{3-(2,5-dioxopyrrol-1-yl)-4-{7-{[2-(trimethylsilyl) ethoxy]methyl}-7H-pyrrolo[2,3-d]pyrimidin-4-yl}-1H-pyrazol-1-yl}propanamide (25 g, 45.3 mmol, 1.0 eq.) in dichloromethane under stirring in an ice bath. After the completion of the addition, the resulting mixture was stirred at room temperature to react for 2 hours. The reaction was quenched with water. The organic layer was washed with water, dried and decolorized with anhydrous magnesium sulfate and activated carbon under stirring. After filtration, the solvent was removed by concentration under reduced pressure to obtain (R)-3-cyclopentyl-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}propionitrile (22.2 g, 41.7 mmol, 92% yield).

$^1$H-NMR (500 MHz, CDCl$_3$): δ8.70 (s, 1H), 8.35 (s, 1H), 7.35 (d, J=3.7 Hz, 1H), 6.66 (d, J=3.7 Hz, 1H), 5.62 (d, J=10.8 Hz, 1H), 5.58 (d, J=10.8 Hz, 1H), 4.30 (m, 1H), 3.50 (m, 2H), 3.09 (dd, J=16.8, 4.3 Hz, 1H), 3.01 (dd, J=16.8, 4.3 Hz, 1H), 2.94 (s, 4H), 2.62 (m, 1H), 1.96 (m, 1H), 1.69 (m, 2H), 1.60 (m, 1H), 1.58 (m, 2H), 1.27 (m, 2H), 0.90 (t, J=8.3 Hz, 2H), −0.06 (s, 9H); HRMS (ESI) calcd. for C$_{27}$H$_{35}$N$_7$O$_3$Si [M+H]$^+$ 534.2643; Found: 534.2657.

Step M: (R)-3-cyclopentyl-3-{3-(2,5-dioxopyrrol-1-yl)-4-{(7-hydroxylmethyl)-7H-pyrrolo[2,3-d]pyrimidin-4-yl}-1H-pyrazol-1-yl}propionitrile A solution of 47% boron trifluoride (34 g, 112.5 mmol, 3.0 eq.) in diethyl ether was added dropwise to a solution of 0.2 M (R)-3-cyclopentyl-3-{3-(2,5-dioxopyrrol-1-yl)-4-{7-{[2-(trimethylsilyl)ethoxy]methyl}-7H-pyrrolo[2,3-d]pyrimidin-4-yl}-1H-pyrazol-1-yl}propionitrile (20 g, 37.5 mmol, 1.0 eq.) in dichloromethane under stirring in an ice bath. After the completion of the addition, the resulting mixture was stirred at room temperature to react for 4 hours. The reaction was quenched with water. The resulting mixture was adjusted with 10% NaOH solution to pH 6-7, and extracted with ethyl acetate. The organic layer was washed with water, washed with saturated salt solution, and dried with anhydrous magnesium sulfate under stirring. After filtration, the filtrate was concentrated under reduced pressure to obtain (R)-3-cyclopentyl-3-[3-(2,5-dioxopyrrol-1-yl)-4-(7-hydroxylmethyl)-7H-pyrrolo[2,3-d]pyrimidin-4-yl)-1H-pyrazol-1-yl]propionitrile (14.4 g, 88.5% yield).

$^1$H-NMR (500 MHz, CDCl$_3$): δ8.54 (s, 1H), 8.31 (s, 1H), 7.31 (d, J=3.7 Hz, 1H), 6.52 (d, J=3.7 Hz, 1H), 5.68 (d, J=10.9 Hz, 1H), 5.61 (d, J=10.9 Hz, 1H), 4.32 (m, 1H), 3.13 (dd, J=17.2, 7.9 Hz, 1H), 3.03 (dd, J=17.2, 4.3 Hz, 1H), 2.94 (s, 4H), 2.62 (m, 1H), 1.98 (m, 1H), 1.74 (m, 1H), 1.65 (m, 1H), 1.64 (m, 2H), 1.30 (m, 1H), 1.29 (m, 2H); HRMS (ESI) calcd. for C$_{22}$H$_{23}$N$_7$O$_3$ [M+H]$^+$ 434.1935; Found: 434.1944.

Step N: (R)-3-[3-amino-4-(7H-pyrrolo[2,3-d]pyrimidin-4-yl)-1H-pyrazol-1-yl]-3-cyclopentyl-propanenitrile (I)

80% Hydrazine hydrate (8.7 g, 138 mmol, 5.0 eq.) was added dropwise to a solution of 0.2 M (R)-3-{3-(2,5-dioxopyrrol-1-yl)-4-{(7-hydroxymethyl)-7H-pyrrolo [2,3-d]pyrimidin-4-yl}-1H-pyrazol-1-yl}-3-cyclopentyl-propanenitrile (12 g, 27.7 mmol, 1.0 eq.) in methanol under stirring at room temperature. After the completion of the addition, the resulting mixture was heated to reflux to react for 8 hours, and concentrated under reduced pressure to evaporate the solvent. The residue was dissolved in ethyl acetate, washed with water, washed with saturated salt solution, and dried with anhydrous sodium sulfate overnight. After filtration, the filtrate was concentrated under reduced pressure to obtain (R)-3-[3-amino-4-(7H-pyrrolo[2,3-d]pyrimidin-4-yl)-1H-pyrazol-1-yl]-3-cyclopentyl-propanenitrile (I) (7.7 g, yield 87%, ee value 99.8%).

$^1$H-NMR (500 MHz, CDCl$_3$): δ11.73 (s, 1H), 8.79 (s, 1H), 8.06 (s, 1H), 7.32 (d, J=3.5 Hz, 1H), 6.62 (d, J=3.5 Hz, 1H), 5.03 (s, 2H), 4.05 (td, J=9.5, 3.5 Hz, 1H), 3.12 (dd, J=17.1, 8.9 Hz, 1H), 2.91 (dd, J=17.1, 3.6 Hz, 1H), 2.54 (m, 1H), 1.74 (m, 1H), 1.63 (m, 4H), 1.27 (m, 1H), 1.26 (m, 2H); HRMS (ESI) calcd. for $C_{17}H_{19}N_7[M+H]^+$ 322.1775; Found: 322.1783.

Example 2: Crystal A of Compound Represented by Formula I

Method 1

2.0 g of the compound represented by formula I obtained in Example 1 was added to 24 mL of anhydrous ethanol. The resulting mixture was heated to reflux to obtain a clear solution, cooled to 0° C. to 5° C., stirred for 4 hours for crystallization, and filtered. The filter cake was washed with 2 mL of anhydrous ethanol, and dried under reduced pressure at 50° C. to obtain 1.62 g of a product (81% yield).

Method 2

4 Parts of 2.0 g of the compound represented by formula I obtained in Example 1 were added to 20 mL of a mixed solvent of anhydrous ethanol and ethyl acetate (4:1, 2:1, 1:1, 1:4), respectively. The resulting mixtures were heated to reflux to obtain a clear solution, cooled to 0° C. to 5° C., stirred for 4 hours for crystallization, and filtered. The filter cakes were washed with 2 mL of ethyl acetate, and dried under reduced pressure at 50° C. to obtain 1.34 g, 1.06 g, 1.00 g, and 1.60 g of products (yield: 67%, 53%, 50%, 80%).

Method 3

2.0 g of the compound represented by formula I obtained in Example 1 was added to 20 mL of a mixed solution of anhydrous ethanol and water (4:1). The resulting mixture was heated to reflux to obtain a clear solution, cooled to 0° C. to 5° C., stirred for 4 hours for crystallization, and filtered. The filter cake was washed with 2 mL of anhydrous ethanol, and dried under reduced pressure at 50° C. to obtain 1.6 g of a product (80% yield).

Method 4

2.0 g of the compound represented by formula I obtained in Example 1 was added to 15 mL of acetone. The resulting mixture was heated to reflux to obtain a clear solution, cooled to 0° C. to 5° C., stirred for 4 hours for crystallization, and filtered. The filter cake was washed with 2 mL of acetone, and dried under reduced pressure at 50° C. to obtain 1.22 g of a product (61% yield).

Method 5

2.0 g of the compound represented by formula I obtained in Example 1 was added to 50 mL of ethyl acetate. The resulting mixture was heated to reflux to obtain a clear solution. The solvent was evaporated by concentration under reduced pressure to obtain 1.98 g of a product (99% yield).

Method 6

2.0 g of the compound represented by formula I obtained in Example 1 was added to 60 mL of dichloromethane. The resulting mixture was heated to reflux to obtain a clear solution. The solvent was evaporated by concentration under reduced pressure to obtain 2.0 g of a product (100% yield).

Method 7

2.0 g of the compound represented by formula I obtained in Example 1 was added to 24 mL of anhydrous ethanol. The resulting mixture was heated to reflux to obtain a clear solution. 120 mL of isopropyl ether was added dropwise. The resulting mixture was cooled to 0° C. to 5° C., stirred for 4 hours for crystallization, and filtered. The filter cake was washed with 2 mL of isopropyl ether, and dried under reduced pressure at 50° C. to obtain 1.56 g of a product (78% yield).

A typical XRD pattern and a typical DSC spectrum of the crystal A of the compound represented by formula I are shown in FIG. 1 and FIG. 2, respectively (Method 1 in Example 2).

Another typical XRD pattern of the crystal A of the compound represented by formula I is shown in FIG. 3 (Method 2 in Example 2, ethanol-ethyl acetate (4:1)).

Still another typical XRD pattern of the crystal A of the compound represented by formula I is shown in FIG. 4 (Method 3 in Example 2).

Example 3: Crystal B of Compound Represented by Formula I 2.0 g of the compound represented by formula I obtained in Example 1 was added to 25 mL of acetonitrile. The resulting mixture was heated to reflux to obtain a clear solution, cooled to 0° C. to 5° C., stirred for 4 hours for crystallization, and filtered. The filter cake was washed with 2 mL of acetonitrile, and dried under reduced pressure at 50° C. to obtain 1.82 g of a product (91% yield).

The crystal B of the compound represented by formula I is an acetonitrilate of the compound represented by formula I. A typical XRD pattern and a typical DSC spectrum of the crystal B of the compound represented by formula I are shown in FIG. 5 and FIG. 6, respectively.

Example 4: Stability Test

The crystal A obtained in Method 1 of Example 2 and the crystal B obtained in Example 3 were placed in an open clean container at 60° C., and sampled for detection on days 5 and 10, respectively. The detection results were compared with the initial detection result of day 0, and the test results were shown in the table below:

| | Item | | | | | |
|---|---|---|---|---|---|---|
| | Crystal A of compound represented by formula I | | | Crystal B of compound represented by formula I | | |
| Date | Day 0 | Day 5 | Day 10 | Day 0 | Day 5 | Day 10 |
| Content (%) | 99.72 | 99.71 | 99.73 | 99.23 | 99.23 | 99.22 |
| Total Impurity (%) | 0.28 | 0.29 | 0.27 | 0.77 | 0.77 | 0.78 |

Example 5 Biological Activity Assays

1. Assay for Enzymatic Activity ($IC_{50}$) of Compounds

A testing platform for kinase activity of JAK2 (wild type) was established based on Homogeneous Time-Resolved Fluorescence (HTRF) assay, and the activities of the compounds were tested using the platform. The compounds were subjected to three-fold gradient dilutions with 100% DMSO with a starting concentration of 1 mM (11 dilutions in total). 4 μL of each dilution was added to 96 μL of reaction buffer (50 mM HEPES, pH 7.4, 10 mM $MgCl_2$, 1 mM EGTA, 0.01% Tween-20, 0.005% BAS, 2 mM DTT) and mixed homogeneously. 2.5 μL of the resulting liquid was then added to a 384-well plate (OptiPlate-384, available from PerkinElmer), and then 5 μL of JAK2 kinase (available from Carna) was added. The mixture was mixed homogeneously by centrifugation. Then 2.5 μL of a mixture of ATP (the final concentration is the corresponding $K_m$ value) and TK peptide (HTRF® KinEASE™-TK, available from Cisbio) was added to initiate the reaction (the total reaction volume is 10 µL). The 384-well plate was placed in an incubator and the reaction was allowed to conduct for 120 min at 23° C. Then the reaction was terminated by adding 5 µL of Eu3+ cryptate-labled anti-phosphotyrosine antibody (available from Cisbio), and 5 µL of Streptavidin-XL-665 (HTRF® KinEASE™-TK, available from Cisbio). The plate was incubated in the incubator for 1 hour, and then the fluorescence values were read on Envision (available from PerkinElmer). The excitation wavelength was 320 nm, and the emission wavelengths for detection were 665 nm and 620 nm. The enzymatic activity was represented by a ratio of the two readouts at the two emission wavelengths. The enzymatic activity for each compound was tested at 11 concentrations, and $IC_{50}$ values of the compounds were obtained by calculating the data using GraFit6.0 software (Erithacus Software). As can be seen from the results, both the $IC_{50}$ value of the compound represented by formula I and the $IC_{50}$ value of the control Ruxolitinib were less than 20 nM.

2. Assay for Efficacy in Mouse Subcutaneous Xenograft Tumor Model

SPF grade Balb/c nude mice are female and 5-6 weeks old. 0.1 mL of the suspension of Ba/F3-JAK2V617F cells in serum-free culture medium (containing $1\times10^7$ cells, 50% MatriGel) was subcutaneously injected into right flank of each mouse. When the average tumor volume reached about 500 mm³, the tumor-bearing mice were sacrificed. The tumor tissues were aseptically picked up, and cut into small pieces, which were subcutaneously implanted into both flanks of Balb/c nude mice. When the average tumor volume reached about 100 mm³, each mouse was marked according to serial numbers, and their tumor sizes and body weights were measured, respectively. These mice were randomly allocated from small to large in terms of tumor volume, and each group of animals was appropriately adjusted to make the average body weights of the groups in a same level. Five groups were negative control group, positive control group, low dose group, moderate dose group, and high dose group, respectively, and each group has five mice. The administration was started on the day of allocation, twice per day for 14 days. During the administration, the tumor volumes and body weights were measured twice per week. The mice were sacrificed at the end of the experiment, and the spleen was isolated and weighed.

During the experiment, the maximum long diameter (L) and the maximum transverse diameter in the vertical direction (W) of the tumor were measured to calculate the tumor volume (V) according to V (mm³)=L×W²/2. Tumor growth inhibition ratio TGI (%)=100%×(1−($T_t$−$T_0$)/($V_t$−$V_0$)), wherein $T_t$ represents the average tumor volume measured every time in the treatment group; $T_0$ represents the average tumor volume of the treatment group when being allocated; $V_t$ represents the average tumor volume measured every time in the control group; and $V_0$ represents the average tumor volume of the control group when being allocated.

The results are shown in the table below.

It can be seen from the data shown in the table that the hydrochloride of the compound represented by formula I was tested for in vivo tumor inhibitory effect in Ba/F3-JAK2V617F tumor-bearing mice model, and it was found to exhibit dose-dependent inhibitory effect on Ba/F3-JAK2V617F tumor growth, and the tumor suppression effect was very remarkable. After the hydrochloride of the compound represented by formula I (100 mg/kg) was orally administered twice per day for 14 days, the tumor growth inhibition ratio (TGI) reached 85.8%, while as for the positive control Ruxolitinib (100 mg/kg) under the equivalent condition, the tumor growth inhibition ratio (TGI) was only 64.5%. The hydrochloride of the compound represented by formula I (50 mg/kg) also exhibited remarkable tumor suppression effect, and the TGI reached 68.4%, which was comparative to the tumor suppression effect of the positive control Ruxolitinib (100 mg/kg).

3. Pharmacokinetic Assay in Adult Male/Female SD Rats

Healthy adult female SD rats were available from Beijing Vital River Laboratory Animal Technology Co., Ltd. The rats were allocated into two groups with three rats per group, and separately orally administered the suspension of a sample to be tested (30 mg/kg) by single intragastric administration. Before the experiment, the animals were fasted overnight, and the fasting time was from 10 hrs before the administration to 4 hrs after the administration. After the administration, blood sampling was conducted at 0.25 hr, 0.5 hr, 1 hr, 2 hrs, 4 hrs, 6 hrs, 8 hrs and 24 hrs. After the animals were narcotized with isoflurane using an anaesthesia machine for small animals, 0.4 mL of whole blood was drawn from fundus venous plexus, and placed in a heparin anticoagulant tube. At 4° C., the sample was centrifuged at 4200 rpm for 5 min, and plasma was transferred to a centrifuge tube and preserved at −80° C. until the analysis was started. The sample in plasma was extracted by the protein precipitation method, and the extract liquid was analyzed by LC/MS/MS.

| Parameter | Unit | Compound represented by formula I | Ruxolitinib[a] |
|---|---|---|---|
| $t_{1/2}$ | hr | 2.20 | 1.22 |
| Tmax | hr | 0.58 | 0.50 |
| Cmax | ng/mL | 2204 | 1143 |
| $AUC_{INFobs}$ | hr * ng/mL | 6316 | 1345 |

Note:
[a]The data are obtained from the pharmacology review published by FDA (U.S. Food & Drug Administration).

The PK data of rats (30 mg/kg PO) showed that the data of the compound represented by formula I were superior to those of Ruxolitinib.

4. Pharmacokinetic Assay in Adult Beagles

Four healthy adult beagles, available from Beijing Marshall Biotechnology Co., Ltd., were used in this study. The study was conducted two times: in the first time, the animals (two males and two females) were administered by single intravenous injection at a dose of 5 mg/kg; in the second time, the same group of animals (two males and two

| Compound | Dose (mg/kg) | Administration Route | Administration Frequency | TGI (%) 3 d | 7 d | 10 d | 14 d |
|---|---|---|---|---|---|---|---|
| Ruxolitinib | 100 | PO | BID | 47.96 | 47.23 | 77.72 | 64.45 |
| Hydrochloride of the compound represented by formula I | 25 | PO | BID | 45.45 | 16.85 | 54.49 | 40.74 |
|  | 50 | PO | BID | 41.77 | 43.60 | 65.19 | 68.40 |
|  | 100 | PO | BID | 91.62 | 79.76 | 89.37 | 85.76 | females) was administered by single intragastric administration at a dose of 10 mg/kg a week later. Before the experiment, the animals which will be subjected to the intragastric administration were fasted overnight, and the fasting time was from 10 hrs before the administration to 4 hrs after the administration. The group of animals which were subjected to the intravenous administration was free to get food. After the administration, blood sampling was conducted at 0.083 hr, 0.25 hr, 0.5 hr, 1 hr, 2 hrs, 4 hrs, 6 hrs, 8 hrs and 24 hrs in the group of intravenous administration. After the administration, blood sampling was conducted at 0.25 hr, 0.5 hr, 1 hr, 2 hrs, 4 hrs, 6 hrs, 8 hrs and 24 hrs in the group of intragastric administration. After the animals were lightly narcotized with isoflurane, 0.4 mL of whole blood was drawn from orbital venous plexus with a glass blood-collecting tube, and placed in a heparin anticoagulant tube. At 4° C., the sample was centrifuged at 4200 rpm for 5 min, and plasma was transferred to a centrifuge tube and preserved at −80° C. until the analysis was started. The sample in plasma was extracted by the protein precipitation method, and the extract liquid was analyzed by LC/MS/MS.

|  |  | IV 5 mg/kg | | | | PO 10 mg/kg | | | |
|---|---|---|---|---|---|---|---|---|---|
|  |  | Compound represented by formula I | | | Ruxolitinib[a] | Compound represented by formula I | | | Ruxolitinib[a] |
| Parameter | Unit | Female | Male | Average | Male | Female | Male | Average | Male |
| $t_{1/2}$ | hr | 3.65 | 3.64 | 3.64 | 2.5 | 3.03 | 3.04 | 3.03 | 2.2 |
| $AUC_{INF\_obs}$ | hr * ng/mL | 11507 | 8192 | 9849 | 13776 | 27445 | 17517 | 22481 | 15716 |
| Cl_obs | mL/hr/kg | 442 | 616 | 529 | 480 | — | — | — | — |
| Vss_obs | mL/kg | 1860 | 2089 | 1974 | 1100 | — | — | — | — |
| $T_{max}$ | hr | — | — | — | — | 1.13 | 0.25 | 0.69 | 2.0 |
| $C_{max}$ | ng/mL | — | — | — | — | 3975 | 3830 | 3903 | 3519 |
| F | % | — | — | — | — | 119 | 107 | 114 | 57 |

Note:
[a]The data are obtained from the pharmacology review published by FDA (U.S. Food & Drug Administration).

The PK data of dogs (10 mg/kg PO, 5 mg/kg IV) showed that the AUC of the compound represented by formula I via IV administration was comparative to that of the positive control Ruxolitinib, but the bioavailability of the compound represented by formula I via oral administration was superior to that of the positive control Ruxolitinib (114% vs 57%).

What is claimed is:

1. A crystal A of a compound represented by formula I:

I wherein an X-ray diffraction pattern of the crystal A of the compound represented by formula I has diffraction peaks at 2θ of 9.35°±0.2°, 11.93°±0.2°, 16.32°±0.2°, 21.23°±0.2°, 23.13°±0.2° and 25.58°±0.2°.

2. A method for preparing the crystal A of the compound represented by formula I according to claim 1, comprising the following steps:
   1) dissolving the compound represented by formula I in a crystallization solvent, wherein the crystallization solvent is selected from methanol, ethanol, n-propanol, isopropanol, n-butanol, isobutanol, t-butanol, ethylene glycol monomethyl ether, diethyl ether, isopropyl ether, methyl t-butyl ether, dioxane, tetrahydrofuran, 2-methyltetrahydrofuran, acetone, 1-butanone, 2-butanone, ethyl acetate, ethyl formate, methyl acetate, isopropyl acetate, dichloromethane, chloroform, water, or a mixed solvent of any two or more of the above solvents; and
   2) crystallizing the compound represented by formula I.

3. The method according to claim 2, wherein the crystallization solvent is ethanol, isopropyl ether, ethyl acetate, acetone, dichloromethane, water, or a mixed solvent of any two or more of the above solvents.

4. A crystalline composition, wherein the crystal A of the compound represented by formula I according to claim 1 accounts for 50% or more, by weight of the crystalline composition.

5. A pharmaceutical composition, comprising an effective amount of the crystal A of the compound represented by formula I according to claim 1.

6. A method for treating a Janus kinase-mediated disease, comprising administering to a mammal in need thereof a therapeutically effective amount of the crystal A of the compound represented by formula I according to claim 1, wherein the Janus kinase-mediated disease is lymphoma or leukemia.

7. A crystal B of a compound represented by formula I:

I wherein an X-ray diffraction pattern of the crystal B of the compound represented by formula I has diffraction peaks at 2θ of 8.97°±0.2°, 9.39°±0.2°, 12.90°±0.2°, 17.70°±0.2°, 20.31°±0.2° and 23.63°±0.2°.

8. The crystal B of the compound represented by formula I according to claim 7 which is an acetonitrilate of the compound represented by formula I, wherein a molar ratio of the compound represented by formula I to acetonitrile is in the range of 1:0.5 to 1:2.0.

9. A method for preparing the crystal B of the compound represented by formula I according to claim 7, comprising the following steps:
   1) dissolving the compound represented by formula I in acetonitrile; and
   2) crystallizing the compound represented by formula I.

10. A crystalline composition, wherein the crystal B of the compound represented by formula I according to claim 7 accounts for 50% or more, by weight of the crystalline composition.

11. A pharmaceutical composition, comprising an effective amount of the crystal B of the compound represented by formula I according to claim 7.

12. A method for treating a Janus kinase-mediated disease, comprising administering to a mammal in need thereof a therapeutically effective amount of the crystal B of the compound represented by formula I according to claim 7, wherein the Janus kinase-mediated disease is lymphoma or leukemia.

13. A method for preparing the crystal B of the compound represented by formula I according to claim 8, comprising the following steps:
   1) dissolving the compound represented by formula I in acetonitrile; and
   2) crystallizing the compound represented by formula I.

14. A crystalline composition, wherein the crystal B of the compound represented by formula I according to claim 8 accounts for 50% or more, by weight of the crystalline composition.

15. A pharmaceutical composition, comprising an effective amount of the crystal B of the compound represented by formula I according to claim 8.

16. A method for treating a Janus kinase-mediated disease, comprising administering to a mammal in need thereof a therapeutically effective amount of the crystal B of the compound represented by formula I according to claim 8, wherein the Janus kinase-mediated disease is lymphoma or leukemia.

17. The crystal A of the compound represented by formula I according to claim 1, wherein an X-ray diffraction pattern of the crystal A of the compound represented by formula I has diffraction peaks at 2θ of 9.35°±0.2°, 11.93°±0.2°, 16.32°±0.2°, 18.82°±0.2°, 20.54°±0.2°, 21.23°±0.2°, 23.13°±0.2° and 25.58°±0.2°.

18. The crystal A of the compound represented by formula I according to claim 1, wherein an X-ray diffraction pattern of the crystal A of the compound represented by formula I has diffraction peaks at 2θ of 9.35°±0.2°, 10.93°±0.2°, 11.93°±0.2°, 14.46°±0.2°, 16.32°±0.2°, 18.82°±0.2°, 20.54°±0.2°, 21.23°±0.2°, 21.66°±0.2°, 23.13°±0.2°, 25.58°±0.2° and 26.34°±0.2°.

19. The crystal B of the compound represented by formula I according to claim 7, wherein an X-ray diffraction pattern of the crystal B of the compound represented by formula I has diffraction peaks at 2θ of 8.97°±0.2°, 9.39°±0.2°, 12.90°±0.2°, 16.54°±0.2°, 17.70°±0.2°, 19.20°±0.2°, 20.31°±0.2°, 22.78°±0.2° and 23.63°±0.2°.

20. The crystal B of the compound represented by formula I according to claim 7 which is an acetonitrilate of the compound represented by formula I, wherein a molar ratio of the compound represented by formula I to acetonitrile is in the range of 1:1.

* * * * *